(12) United States Patent
Hsu et al.

(10) Patent No.: US 9,097,726 B2
(45) Date of Patent: *Aug. 4, 2015

(54) METHODS OF EVALUATING BAFF

(71) Applicant: Biogen Idec MA Inc., Cambridge, MA (US)

(72) Inventors: Yen-Ming Hsu, Lexington, MA (US); Susan Kalled, Concord, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/179,820

(22) Filed: Feb. 13, 2014

(65) Prior Publication Data

US 2014/0273019 A1 Sep. 18, 2014

Related U.S. Application Data

(62) Division of application No. 13/791,293, filed on Mar. 8, 2013, now Pat. No. 8,685,657, which is a division of application No. 13/477,754, filed on May 22, 2012, now Pat. No. 8,415,111, which is a division of application No. 12/092,861, filed as application No. PCT/US2006/043196 on Nov. 7, 2006, now Pat. No. 8,202,698.

(60) Provisional application No. 60/734,602, filed on Nov. 8, 2005.

(51) Int. Cl.
*G01N 33/68* (2006.01)
*C07K 16/28* (2006.01)
*G01N 33/564* (2006.01)

(52) U.S. Cl.
CPC ........ *G01N 33/6863* (2013.01); *C07K 16/2875* (2013.01); *G01N 33/564* (2013.01)

(58) Field of Classification Search
None
See application file for complete search history.

(56) References Cited

U.S. PATENT DOCUMENTS

| 8,202,698 B2 | 6/2012 | Hsu et al. |
| 8,415,111 B2 | 4/2013 | Hsu et al. |
| 8,685,657 B2 | 4/2014 | Hsu et al. |
| 2003/0223996 A1 | 12/2003 | Ruben et al. |
| 2005/0070694 A1 | 3/2005 | Gelfanova et al. |

OTHER PUBLICATIONS

International Search Report and Written Opinion for PCT/US2006/043196, mailed Apr. 25, 2007 from International Searching Authority of the European Patent Office.
Cheema et al., "Elevated Serum B Lymphocyte Stimulator Levels in Patients with Systemic Immune-Based Rheumatic Diseases," Arthritis and Rheumatism, 44:1313-1319 (2001).
Groom et al., "Association of BAFF/Blys Overexpression and Altered B Cell Differentiation with Sjorgen's Syndrome," Journal of Clinical Investigation, 109:59-68 (2002).
Krumbholz et al., "BAFF is produced by astrocytes and up-regulated in multiple sclerosis lesions and primary central nervous system lymphoma", The Journal of Experimental Medicine, vol. 201, No. 2, pp. 195-200, published online Jan. 10, 2005.
Zhang et al., "Cutting Edge: A Role for B Lymphocyte Stimulator in Systemic Lupus Erythematosus," Journal of Immunology, 166:6-10 (2001).

*Primary Examiner* — Jacob Cheu
(74) *Attorney, Agent, or Firm* — Finnegan, Henderson, Farabow, Garrett & Dunner, LLP

(57) ABSTRACT

The present disclosure provides compositions and methods relating to the evaluation of BAFF in a biological sample from a subject.

17 Claims, 1 Drawing Sheet

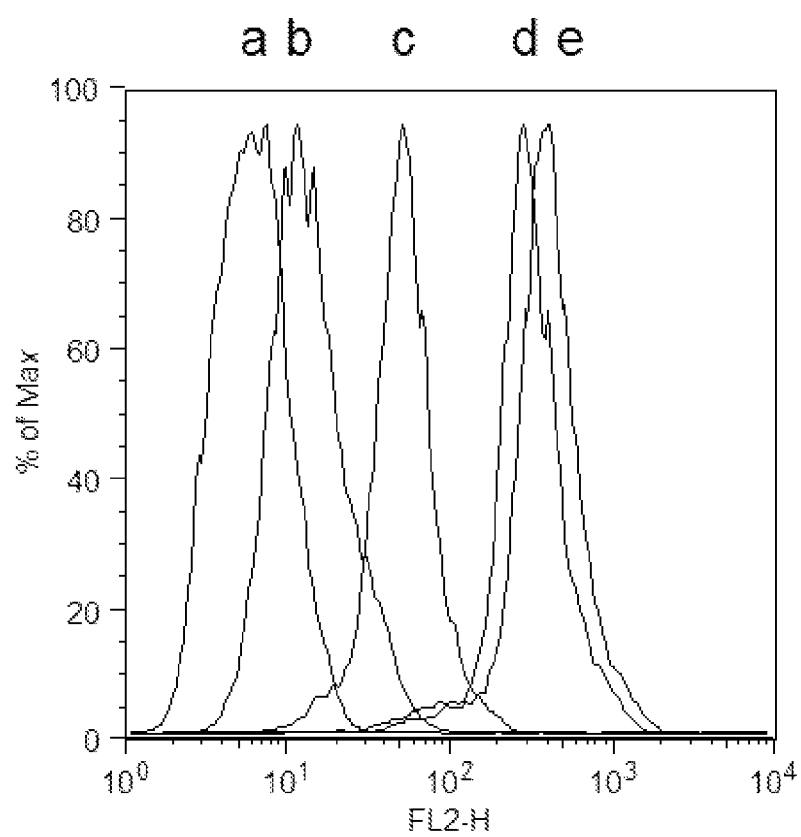

METHODS OF EVALUATING BAFF

This is a continuation of application Ser. No. 13/791,293, filed Mar. 8, 2013, which is a divisional of application Ser. No. 13/477,754, filed May 22, 2012, which is a divisional of application Ser. No. 12/092,861, filed Jun. 28, 2008, which is a National Stage Entry of International Application No. PCT/US06/43196, filed Nov. 7, 2006, which claims the benefit of U.S. Provisional Application No. 60/734,602, filed Nov. 8, 2005, all of which are incorporated herein by reference.

FIELD OF THE INVENTION

The present invention relates to BAFF, a B-cell activating factor in the TNF family. The invention provides anti-BAFF antibodies and methods of detecting BAFF in a biological sample, such as a tissue sample, blood, or serum.

BACKGROUND

BAFF (B cell-activating factor in the TNF family), also known as BLyS, TALL-1, THANK, and zTNF4, is implicated a number of autoimmune and lymphoproliferative disorders. For a review, see, e.g., Kalled et al., Curr. Dir. Autoimmun. 8:206-242 (2005). BAFF is expressed in macrophages, monocytes, dendritic cells and T cells and is critical for the survival of B cells. Moore et al., Science 285:260-263 (1999); Mukhopadhyay et al., J Biol. Chem. 274:15978-15981 (1999); Gross et al., Nature 404:995-999 (2000); Shu et al., J. Leukoc. Biol. 65:680-683 (1999). BAFF is a type II transmembrane protein that can be proteolytically cleaved between Arg 133 and Ala 134 and released as a soluble protein. Moore et al., Science 285:260-263 (1999); Schneider et al., J. Exp. Med. 189:1747-1756 (1999). To date, three receptors for BAFF have been identified: TACI, BCMA, and BR3 (also known as BAFF-R).

In vivo, BAFF can exist as a transmembrane protein or a soluble protein, and can be bound or unbound to a receptor. Thus, BAFF is distributed among a variety of pools, including free soluble BAFF, receptor-bound soluble BAFF, transmembrane BAFF, and receptor-bound transmembrane BAFF.

Excess BAFF has been implicated in several disease states, including Sjogren's Syndrome, rheumatoid arthritis and lupus (reviewed in Kalled, 2005, Immunol Rev. 204:43-54). Some known methods for detection of BAFF in biological samples utilize antibodies that detect unbound BAFF (e.g., free soluble BAFF, e.g., in serum). However, because BAFF may also be complexed with receptor, such methods do not identify those patients that may have normal levels of unbound BAFF but may have abnormal BAFF distribution or abnormal or increased levels of receptor-bound BAFF or membrane bound BAFF and/or total BAFF. New methods are needed to identify such patients, e.g., as candidates for therapy (e.g., anti-BAFF therapy) and/or to monitor such patients (e.g., for BAFF response).

SUMMARY

The invention provides methods and compositions for evaluating BAFF status, levels, and/or distribution. Included are methods to evaluate the distribution of BAFF among distinct physiological pools, methods of determining the total BAFF in a biological sample, and related methods and compositions. In some embodiments, the methods can be performed on a biological sample (e.g., tissue, blood, or serum) that may be obtained from a healthy mammal (e.g., a human or a rodent) or from a mammal at any of stage of disease (e.g., autoimmune disease and lymphoproliferative disorders).

The invention relates, at least in part, to antibodies that bind to BAFF independent of its physiological state, i.e., independent of whether BAFF is complexed with receptor(s) or not. One such antibody is a monoclonal anti-BAFF antibody referred to herein as B4H7. B4H7 detects free BAFF and BAFF bound to receptor. Because the binding of the antibody to BAFF is substantially independent of the physiological state of the BAFF, the antibody allows assessment of total BAFF and determination of the proportion of BAFF distributed across various physiological pools in a given biological sample.

BAFF can form multimers, e.g., trimers. Zhukovsky et al., Nature 427:413-414 (2004). For the purposes of this disclosure, the phrase, "anti-BAFF antibody that binds to BAFF independent of whether BAFF is bound to a receptor" refers to an antibody that binds to a BAFF monomer (i.e., a free monomer or a monomeric subunit of a BAFF multimer) independent of whether that BAFF monomer is bound to a receptor. Such antibodies are characterized by one or more of the following features:

(1) the affinity of the antibody for free BAFF and its affinity for BAFF bound to receptor are substantially the same (i.e., the affinity constants differ by no more than 30%);
(2) the anti-BAFF antibody binds to an epitope of BAFF outside of the binding sites for BCMA, TACI, and BR3;
(3) the anti-BAFF antibody competitively inhibits antibody B4H7 from binding to BAFF;
(4) the anti-BAFF antibody is competitively inhibited from binding to BAFF by antibody B4H7;
(5) the anti-BAFF antibody binds to the same site or epitope as antibody B4H7;
(6) the affinity of the anti-BAFF antibody to BAFF bound to receptor is at least $10^6$ $M^{-1}$;
(7) the anti-BAFF antibody comprises at least one complementarity determining region (CDR) that is identical to a corresponding CDR in B4H7; and
(8) the anti-BAFF antibody detects receptor-bound BAFF (e.g., BR3, TACI and/or BCMA-bound BAFF) at least 2 times, 3 times, 4 times, 5 times, 8 times, or 10 times better than antibody A9C9, e.g., qualitatively, e.g., by flow cytometry analysis (e.g., in a FACS™ assay).

The invention also provides methods of making anti-BAFF antibodies that bind to BAFF independent of its physiological state, e.g., independent of whether BAFF is bound to a receptor. For example, the invention provides methods of making an anti-BAFF antibody that binds to BAFF independent of whether BAFF is bound to a receptor comprising determining whether an anti-BAFF antibody possesses one or more of the features listed above.

Further provided are methods of using anti-BAFF antibodies of the invention. Such methods include methods of evaluating total BAFF and/or the distribution of BAFF in a biological sample (e.g., the relative levels of receptor-bound BAFF).

A method of evaluating total BAFF includes the steps of:
(a) contacting a biological sample (e.g., from a subject such as a patient) with an anti-BAFF antibody that binds BAFF independent of its physiological state, e.g., independent of whether BAFF is bound to a receptor; and (b) evaluating the amount of BAFF bound by the antibody. The amount of BAFF determined in (b) indicates total BAFF in the biological sample. The evaluation can be performed by a quantitative or qualitative technique, e.g., ELISA (e.g., for a biological fluid sample such as serum, urine, synovial fluid, cerebrospinal fluid (CSF), bronchoalveolar lavage (BAL) fluid, or saliva); immunohistochemistry (e.g., for a tissue sample such as a biopsy, e.g., a kidney, salivary gland, synovial joint, thyroid, or brain biopsy); or flow cytometry techniques such as FACS™ (e.g., for blood or other cellular fluids such as BAL, CSF, or synovial fluid).

In one embodiment, this method can be used, e.g., to identify a patient that is a candidate for BAFF antagonist therapy, such as an inhibitory anti-BAFF antibody, a soluble BAFF receptor, or an inhibitory anti-BAFF receptor antibody. Such a patient may not have increased levels of free BAFF, e.g., serum BAFF, and thus may not be identifiable by prior art methods. A greater level of total BAFF bound by the antibody, compared to a reference value, can indicate that the subject is a candidate for a BAFF antagonist therapy.

In another embodiment, the method can be used to monitor free BAFF levels in a subject who is undergoing a therapy (e.g., a BAFF antagonist therapy or other therapy such as anti-TNF therapy) for an immune disease such as an autoimmune disease, e.g., rheumatoid arthritis (RA), lupus, multiple sclerosis (MS), Sjogren's Syndrome, or Graves' Disease. The monitoring can be performed, e.g., before and/or after a treatment, e.g., at specified intervals after treatment. A reduced level of total BAFF bound by the antibody, compared to a reference value, such as a pre-therapy control value, can indicate that the subject is responsive to a BAFF antagonist therapy. This method also allows for evaluation of BAFF levels in cases where a subject is being treated with a decoy BAFF receptor (e.g., BR3-Fc, TACI-Fc or BCMA-Fc) that sequesters BAFF.

In yet another embodiment, the method can be used to determine if a test composition affects the levels of BAFF in a biological sample from a subject, e.g., an experimental animal or a human subject. A reduced level of total BAFF bound by the antibody, compared to a reference value, can indicate that the composition is effective as a BAFF antagonist therapy.

In another aspect, a method of evaluating the distribution of BAFF includes: (a) contacting a biological sample with a first anti-BAFF antibody, which binds BAFF independent of its physiological state, e.g., independent of whether BAFF is bound to a receptor; (b) contacting the sample with a second anti-BAFF antibody, which preferentially binds free BAFF (e.g., free soluble BAFF and/or free transmembrane BAFF) over BAFF bound to receptor; and (c) comparing the binding of the first antibody and the binding of the second antibody to BAFF in the sample. The comparison in (c) indicates the distribution of BAFF among various physiological pools in the sample. For example, binding of the first anti-BAFF antibody in the sample represents receptor-bound and free BAFF in the sample, and the difference between the binding of the first and second antibodies represents receptor-bound BAFF in the sample. In one embodiment, the method is performed by immunohistochemistry or by flow cytometry (e.g., FACS™) wherein the first and second antibodies are differentially labeled and sorted from the same sample.

In one embodiment, this method can be used, e.g., to identify a patient that is a candidate for BAFF antagonist therapy, such as an inhibitory BAFF antibody, a soluble BAFF receptor, or an inhibitory anti-BAFF receptor antibody. Such a patient who has increased levels of receptor-bound BAFF as determined by the methods disclosed herein may not have increased levels of free BAFF, e.g., serum BAFF.

In another embodiment, the method can be used to monitor receptor-bound BAFF levels in a subject who is undergoing a therapy (e.g., a BAFF antagonist therapy or other therapy such as anti-TNF therapy) for an immune disease such as an autoimmune disease, e.g., RA, lupus, MS, Sjogren's Syndrome, or Graves' Disease. A reduced level of receptor-bound BAFF (e.g., BR3 bound-BAFF), compared to a reference value, such as a pre-therapy control value, can indicate that the subject is responsive to a BAFF antagonist therapy. The monitoring can be performed, e.g., before and/or after a treatment, e.g., at specified intervals after treatment. This method also allows for evaluation of BAFF distribution in cases where a subject is being treated with a decoy BAFF receptor (e.g., BR3-Fc or BCMA-Fc) that sequesters BAFF.

In another embodiment, the method can be used to determine if a test composition affects the levels of receptor-bound BAFF in a biological sample from a subject, e.g., an experimental animal or a human subject. A reduced level of receptor-bound BAFF, compared to a reference value, can indicate that the composition is effective as a BAFF antagonist therapy.

In another aspect, the invention provides a method of evaluating the distribution of BAFF in a subject, including: (a) contacting a first biological sample from the subject with a first anti-BAFF antibody that binds BAFF independent of its physiological state, e.g., independent of whether BAFF is bound to a receptor; (b) contacting a second biological sample from the subject, of the same type as the first, with a second anti-BAFF antibody, which preferentially binds free BAFF over BAFF bound to receptor; and (c) comparing the binding of the first antibody and the binding of the second antibody to BAFF in the two samples. The comparison in (c) indicates the distribution of BAFF among various physiological pools in the samples. For example, binding of the first anti-BAFF antibody in the sample represents receptor-bound and free BAFF in the sample, and the difference between the binding of the first and second antibodies represents receptor-bound BAFF in the sample. In one embodiment, steps (a) and (b) are performed with the same technique. In another embodiment, steps (a) and (b) are performed with different techniques, e.g., step (a) can be performed by ELISA and step (b) can be performed by flow cytometry in whole blood or other biological fluids and/or by immunohistochemistry. In one embodiment, the first and second biological samples are from the same source (e.g., the subject's blood). As described above for the other methods, this method can be used to identify a patient candidate for BAFF antagonist therapy, to monitor a subject's BAFF response to a therapeutic regimen, and/or to screen for compounds that may modulate receptor-bound BAFF levels in a subject.

The invention further provides methods of evaluating the ability of a test compound or composition, or a therapeutic compound or composition, to modulate the distribution of BAFF. One such method includes:
  (a) administering a test compound or composition to a mammal;
  (b) obtaining a biological sample from the mammal;
  (c) contacting the sample with a first anti-BAFF antibody, which binds BAFF independent of its physiological state, e.g., independent of whether BAFF is bound to a receptor;
  (d) contacting the sample with a second anti-BAFF antibody, which preferentially binds free BAFF over BAFF bound to receptor;
  (e) detecting binding of the first antibody and the second antibody to BAFF in the sample; and
  (f) comparing the binding of the first antibody and the second antibody in the biological sample to the binding of the first and second antibodies, respectively, in a control sample.

A difference in binding attributable to the test compound or composition or therapeutic compound or composition indicates that the compound or composition is effective in modulating the distribution of BAFF (e.g., BR3-bound BAFF) in the mammal. In some embodiments, the control sample is obtained from the same mammal prior to the administration of the compound or composition to be tested. The method can be used, e.g., to screen for compounds or compositions that modulate BAFF levels or distribution, or to monitor the effects of a therapeutic composition, e.g., in a patient, on BAFF levels or distribution. In one embodiment, a patient is considered responsive to the therapeutic composition if the patient exhibits changes (e.g., decreases) in BAFF levels as a result of administration of the composition.

The invention also provides a method of evaluating the ability of a test compound or composition or therapeutic compound or composition to modulate the distribution of BAFF, the method including:
(a) administering a test compound or composition to a mammal;
(b) obtaining a first biological sample and a second biological sample, both of the same type, from the mammal;
(c) contacting the first biological sample with a first anti-BAFF antibody, which binds BAFF independent of its physiological state, e.g., independent of whether BAFF is bound to a receptor;
(d) contacting the second biological sample with a second anti-BAFF antibody, which preferentially binds free BAFF over BAFF bound to receptor;
(e) detecting binding of the first antibody and the second antibody to BAFF in the two biological samples; and
(f) comparing the binding of the first antibody and second antibody in the two biological samples to the binding of the first and second antibodies, respectively, in one or more control samples.

A difference in binding attributable to the test compound or composition indicates that the compound or composition is effective in modulating the distribution of BAFF in the mammal.

The invention also provides a method of evaluating the ability of a test compound or composition or therapeutic compound or composition to modulate total BAFF, the method including:
(a) administering a test compound or composition or therapeutic compound or composition to a mammal;
(b) obtaining a biological sample from the mammal;
(c) contacting the biological sample with an anti-BAFF antibody that binds BAFF independent of its physiological state, e.g., independent of whether BAFF is bound to a receptor;
(d) evaluating the amount of BAFF bound by the antibody in the biological sample; and
(e) comparing the amount of BAFF bound by the antibody in the biological sample with the amount of BAFF bound by the antibody in a control sample.

The amount of BAFF bound by the antibody indicates total BAFF in the sample. A difference in binding attributable to the test compound or composition indicates that the compound or composition is effective in modulating total BAFF in the mammal.

In any of the methods described herein, the result of the method (e.g., the evaluation of the amount or distribution of BAFF in a subject) can be evaluated against a reference value, e.g., a predetermined threshold control value, the relative levels of total BAFF from a control subject (e.g., a healthy control), or relative levels of total BAFF from the same subject at a previous time (e.g., before diagnosis of a disease, before exacerbation of a disease, during a remission period of a disease, or before beginning a therapeutic regimen).

The methods of the invention may include quantitative and/or qualitative analysis of binding between BAFF and an anti-BAFF antibody. In many cases, the methods described herein include evaluations that are qualitative rather than determinations of absolute levels. For example, in one embodiment, the levels of receptor-bound BAFF in a particular sample are evaluated as relative levels compared to free BAFF in the sample, and/or referenced to relative levels in a control sample. In some embodiments, this analysis may be carried out using ELISA, FACS™, and/or immunohistochemistry.

The invention further provides specific anti-BAFF antibodies that, unlike B4H7, do not bind substantially equally to free BAFF and to BAFF bound to receptor. Such antibodies are referred to herein as A11C3, A9C9, and AE5. The invention further provides methods of making and methods of using such antibodies.

Biological Deposits

A hybridoma expressing B4H7 was deposited on May 18, 2006, at American Tissue Culture Collection (ATCC) under Deposit Designation Number PTA-7602. The address of the depository is 10801 University Blvd, Manassas, Va. 20110, U.S.A.

BRIEF DESCRIPTION OF THE DRAWING

FIG. 1 is a fluorescence trace for a FACS experiment testing the ability of anti-BAFF antibodies (B4H7 and A9C9) and control mouse IgG to bind to BAFF bound to BJAB cells expressing BR3. Profiles are labeled as follows: (a) unstained cells; (b) biotinylated BAFF+control mouse IgG+mouse anti-IgG PE; (c) biotinylated BAFF+A9C9+anti-mouse IgG PE; (d) biotinylated BAFF only+SA-PE; and (e) biotinylated BAFF+B4H7+anti-mouse-PE.

DETAILED DESCRIPTION

BAFF and its Receptors

BAFF knockout mice lack mature B cells in the periphery, showing that BAFF is required for B cell development in vivo. Gross et al., Immunity 15: 289-302 (2001); Schiemann et al., Science 293:2111-2114 (2001). Animals overexpressing BAFF display symptoms of autoimmune disorders (Mackay, J. Exp. Med. 190:1697-1710 (1999)) and soluble BAFF is detected in the blood of patients with various autoimmune disorders. Gross et al., Nature 404:995-999 (2000); Groom et al., J. Clin. Invest. 109:59-68 (2002); Zhang et al., J. Immunol. 166:6-10 (2001); Cheema et al., Arthritis Reum. 44:1313-1319 (2001). BAFF has also been reported to form biologically active heteromers with APRIL (A Proliferation-Inducing Ligand), a related TNF family ligand. These heterotrimers are present in serum samples from patients with systemic immune-based rheumatic diseases. Roschke et al., J. Immunol. 169:4314-4321 (2002).

BAFF co-stimulates the proliferation of B cells in the presence of anti-IgM (Schneider et al., J. Exp. Med. 189:1747-1756 (1999)) and is able to signal through three receptors: BCMA (B cell maturation antigen), TACI (transmembrane activator and cyclophilin ligand interactor, and BR3 (BAFF receptor 3, also known as BAFF-R). Fusion proteins of these receptors with the CH1, CH2, and hinge region of human IgG1 block the proliferation of B cells induced by BAFF. Gross et al., Nature 404:995-999 (2000); Gross et al., Immunity 15: 289-302 (2001); Thompson et al., J. Exp. Med. 192: 129-135 (2000); Thompson et al., Science 293:2108-2111 (2001).

BCMA and TACI bind to both BAFF and APRIL. Gross et al., Nature 404:995-999 (2000); Wu et al., J. Biol. Chem. 275:35478-35485 (2000); Xia et al., J. Exp. Med. 192:137-143 (2000); Yan et al., Nat. Immunol. 1:37-41 (2000); Yu et al., Nat. Immunol. 1:252-256 (2000). BR3 is expressed in all peripheral B cells and is specific for BAFF, i.e., unlike BCMA and TACI, BR3 does not bind APRIL. Mice lacking BR3 have a similar phenotype to BAFF knockout mice. Thompson et al., Science 293:2108-2111 (2001); Yan et al., Curr. Biol. 11:1547-1552 (2001). Recently, studies with monomeric receptors have shown that BAFF binds BR3 with 100-fold higher affinity than it binds BCMA. Rennert et al., J. Exp. Med. 192:1677-1684 (2000); Patel et al., J. Biol. Chem. 279:16727-16735 (2004); Day et al., Biochemistry 44:1919-1931 (2005).

The crystal structures of BAFF bound to BCMA and BR3, respectively, have been solved. Liu et al., Nature 423:49-56 (2003); Gordon et al., Biochemistry 42:5977-5983 (2003); Kim et al., Nat. Struct. Biol. 10:342-348 (2003); PCT Application Publication No. WO 03/035846. Liu et al. found that 12 residues in BAFF are involved in binding BCMA (Tyr 163, Leu 200, Tyr 206, Leu 211, Arg 231, Ile 233, Leu 240, Pro 264, Arg 265, Glu 266, Asp 273, and Asp 275), while 14 residues are involved in binding BR3 (Tyr 163, Leu 200, Asp 203, Tyr 206, Leu 211, Arg 231, Ile 233, Leu 240, Pro 264, Arg 265, Glu 266, Asn 267, Asp 273, and Asp 275). In view of the nearly identical sets of BAFF residues involved in BCMA and BR3 binding, Liu et al. speculate that the same residues are involved in BAFF-TACI binding. Liu et al., Nature 423:49-56 (2003). This conclusion is supported by a report that the overall structure of the BAFF-binding domain of TACI is similar to the structure of BCMA and that TACI binds APRIL in a manner similar to the way BCMA binds BAFF. Hymowitz et al., J. Biol. Chem. 280:7218-7227 (2005).

The amino acid sequences of naturally occurring full-length human BAFF, BCMA, TACI, and BR3 are available under GenBank™ accession numbers AAD25356, BAB60895, AAP57629, and AAK91826, respectively.

Physiological Pools of BAFF

BAFF can exist in transmembrane forms and cleaved, soluble forms. Further, both forms of BAFF are capable of ligand:receptor binding. Thus, BAFF is found in a variety of pools, including (1) free transmembrane BAFF, (2) free soluble BAFF, (3) transmembrane BAFF:transmembrane receptor, (4) soluble BAFF:transmembrane receptor.

Antibodies

One exemplary antibody of the invention, monoclonal antibody B4H7, binds BAFF independent of BAFF's physiological state. E.g., it binds free BAFF and BAFF bound to receptor substantially equally. B4H7 binds to receptor-bound BAFF regardless of whether BAFF or the receptor is soluble or membrane-bound. B4H7, and other antibodies possessing similar characteristics as described herein, allow for assessment of total BAFF in a sample and determination of the distribution of BAFF among various physiological pools.

In addition to B4H7, the invention also includes anti-BAFF antibodies characterized by one or more of the following features:

(1) the affinity of the antibody for free BAFF and its affinity for BAFF bound to receptor are substantially the same (i.e., the affinity constants differ by no more than 30%);
(2) the anti-BAFF antibody binds to an epitope of BAFF outside of the binding sites for BCMA, TACI, and BR3;
(3) the anti-BAFF antibody competitively inhibits antibody B4H7 from binding to BAFF;
(4) the anti-BAFF antibody is competitively inhibited from binding to BAFF by antibody B4H7;
(5) the anti-BAFF antibody binds to the same site as antibody B4H7;
(6) the affinity of the anti-BAFF antibody to BAFF bound to receptor is at least $10^6$ $M^{-1}$; and
(7) the anti-BAFF antibody comprises at least one complementarity determining region (CDR) that is identical to a corresponding CDR in B4H7.
(8) the anti-BAFF antibody detects receptor-bound BAFF (e.g., BR3, TACI and/or BCMA-bound BAFF) at least 2 times, 3 times, 4 times, 5 times, 8 times, or 10 times better than antibody A9C9, e.g., qualitatively, e.g., by flow cytometry (e.g., in a FACS assay).

In certain embodiments, levels of binding that differ by no more than 30% or that are the same within detection limits of a given method are considered "substantially equal". In one embodiment, the levels of binding differ by no more than 25%. In one embodiment, the levels of binding differ by no more than 20%. In one embodiment, the levels of binding differ by no more than 15%. In one embodiment, the levels of binding differ by no more than 10%. In one embodiment, the levels of binding differ by no more than 5%. In one embodiment, the levels of binding differ by no more than 1%.

ELISA or another suitable assay may be used to determine the levels of binding of an anti-BAFF antibody to free BAFF and to BAFF bound to receptor. In one example, the affinity constants of the antibody with respect to free BAFF and BAFF bound to receptor differ by no more than 30% are considered substantially equal. In another example, values differing by less than 2 points on a 5-point Likert scale, or a similar scale, are considered substantially equal. In yet another example, levels of binding that are the same within detection limits of a given methods are considered substantially equal.

In one embodiment, an anti-BAFF antibody that is competitively inhibited from binding to BAFF by antibody B4H7 and/or competitively inhibits antibody B4H7 from binding to BAFF is considered to bind to the same site as antibody B4H7.

The invention also provides methods of selecting an anti-BAFF antibody. Exemplary methods comprise contacting BAFF with receptor, thus yielding BAFF bound to receptor. The receptor may be recombinant receptor or expressed on the surface of cells, for example. (Whether BAFF is bound may be assessed as described herein, i.e., by contacting BAFF with differentially tagged or labeled receptor and determining whether further binding of receptor to BAFF can be detected. If binding of the differentially tagged or labeled receptor is not detectable, BAFF is already bound to receptor.) The antibody under consideration is then allowed to contact BAFF bound to receptor and free BAFF. Binding of the antibody to receptor-bound BAFF and free BAFF is detected using any suitable assay. The antibody is selected if it demonstrates the desired binding properties, e.g., binding substantially equally to free BAFF and BAFF bound to receptor.

The invention further provides specific anti-BAFF antibodies that, unlike B4H7, do not substantially equally bind free BAFF and BAFF bound to receptor. As shown in the Examples, such antibodies include those referred to herein as A11C3, A9C9, and AE5. The invention further provides methods of making, and methods of using such antibodies.

The term "antibody," as used herein, refers to immunoglobulin molecules and immunologically active portions of immunoglobulin molecules, i.e., molecules that contain an antigen binding site that specifically binds (immunoreacts with) an antigen, such as a BAFF polypeptide, including specific BAFF structures. The term antibody encompasses any polypeptide comprising an antigen-binding site of an immunoglobulin regardless of the source, species of origin, method of production, and characteristics. As a non-limiting example, the term "antibody" includes human, orangutan, monkey, mouse, rat, goat, sheep, and chicken antibodies. The term includes, but is not limited to, polyclonal, monoclonal, human, humanized, single-chain, chimeric, synthetic, recombinant, hybrid, mutated, resurfaced, and CDR-grafted antibodies. For the purposes of the present invention, it also includes, unless otherwise stated, antibody fragments such as Fab, F(ab')$_2$, Fv, scFv, Fd, dAb, and other antibody fragments that retain the antigen-binding function. A "monoclonal antibody," as used herein, refers to a population of monospecific antibody molecules that contain a particular antigen binding site and are capable of specifically binding to a particular epitope.

Antibodies can be made, for example, via traditional hybridoma techniques (Kohler et al., Nature 256:495-499 (1975)), recombinant DNA methods (U.S. Pat. No. 4,816,567), or phage display techniques using antibody libraries (Clackson et al., Nature 352:624-628 (1991); Marks et al., J. Mol. Biol. 222:581-597 (1991). For various other antibody production techniques, see Antibody Engineering, 2nd ed., Borrebaeck, Ed., Oxford University Press, 1995; Antibodies: A Laboratory Manual, Harlow et al., Eds., Cold Spring Harbor Laboratory, 1988; and Antibody Engineering: Methods and Protocols (Methods in Molecular Biology), Lo, Ed., Humana Press, 2003. An antibody may comprise a heterologous sequence such as an affinity tag, for example.

The term "antigen-binding domain" refers to the part of an antibody molecule that comprises the area specifically binding to or complementary to a part or all of an antigen. An antigen-binding domain may be provided by one or more antibody variable domains (e.g., a so-called Fd antibody fragment consisting of a $V_H$ domain). An antigen-binding domain comprises an antibody light chain variable region ($V_L$) and an antibody heavy chain variable region ($V_H$). Where an antigen is large, an antibody may only bind to a particular part of the antigen. The "epitope" or "antigenic determinant" is a portion of an antigen molecule that is responsible for specific interactions with the antigen-binding domain of an antibody.

In some embodiments, the antibodies, polypeptides, or other compounds of the invention are isolated. The term "isolated" refers to a molecule that is substantially free of its natural environment. For instance, an isolated protein is substantially free of cellular material or other proteins from the cell or tissue source from which it was derived. The term also refers to preparations where the isolated protein is at least 70-80% (w/w) pure; or at least 80-90% (w/w) pure; or at least 90-95% pure; or at least 80%, 85%, 90%, 95%, 96%, 97%, 98%, 99%, or 100% (w/w) pure. In some embodiments, the isolated molecule is sufficiently pure for pharmaceutical compositions.

Certain embodiments of the invention involve consideration of antibody affinity or binding constants. Exemplary binding constants include, but are not limited to, the equilibrium binding constant, $K_d$, and the kinetic binding constant, $k_d$. Techniques for determining binding constants, e.g., surface plasmon resonance (Biacore™), are known in the art.

In certain embodiments, comparing the levels of binding of the antibodies (e.g., as determined by FACS™ or ELISA assay) indicates the level of BAFF bound to receptor in the sample, i.e., the level of binding of the antibody that binds BAFF independent of its physiological state minus the level of binding of the antibody that preferentially binds free BAFF over BAFF bound to receptor indicates the level of BAFF bound to receptor.

A "biological sample" is biological material collected from cells, tissues, organs, or organisms. Exemplary biological samples include serum, blood, plasma, biopsy sample, tissue sample, cell suspension, biological fluid, saliva, oral fluid, cerebrospinal fluid, amniotic fluid, milk, colostrum, mammary gland secretion, lymph, urine, sweat, lacrimal fluid, gastric fluid, synovial fluid, mucus, and other samples and clinical specimens.

If the biological sample is representative of only a subset of the BAFF pools, evaluation of the sample provides a direct assessment of those pools. For example, if the biological sample is serum, only free soluble BAFF (and soluble BAFF:soluble receptor in cases where the sample is from a patient being treated with a decoy receptor such as BCMA-Fc, TACI-Fc or BR3-Fc) are directly represented in the sample. Thus, in serum, the level of binding of the antibody that binds BAFF independent of its physiological state indicates the total level of BAFF in serum. Similarly, the level of binding of the antibody that preferentially binds free BAFF over BAFF bound to receptor indicates the level of free soluble BAFF, and the difference in binding between the two antibodies indicates the level of soluble BAFF:soluble receptor. When compared to a reference, such as the difference in binding between the two antibodies in a control sample, increased levels can be indicative, e.g., of candidacy for a BAFF antagonist therapy.

Alternatively, if the sample comprises cells but little or no extracellular fluid, the represented pools may include free transmembrane BAFF, transmembrane BAFF:transmembrane receptor, and soluble BAFF:transmembrane receptor. In this embodiment, the level of binding of the antibody that binds BAFF independent of its physiological state indicates the total level of BAFF among these pools, the level of binding of the antibody that preferentially binds free BAFF over BAFF bound to receptor indicates the level of free transmembrane BAFF, and the difference between the two antibodies (e.g., in a FACS™ assay or immunohistochemistry assay) indicates the level of BAFF among the following pools: transmembrane BAFF:transmembrane receptor, and soluble BAFF:transmembrane receptor. Again, when compared to a reference, such as the difference in binding between the two antibodies in a control sample, increased levels can be indicative, e.g., of candidacy for a BAFF antagonist therapy. Finally, if the biological sample is representative of all BAFF pools, the level of binding of the antibody that binds BAFF independent of its physiological state indicates the total level of BAFF. In this embodiment, the level of binding of the antibody that preferentially binds free BAFF over BAFF bound to receptor indicates the total level of BAFF among the free soluble BAFF and free transmembrane BAFF pools, and the difference between the two antibodies indicates the total level of BAFF among the transmembrane BAFF:transmembrane receptor, and soluble BAFF:transmembrane receptor pools.

In most cases, the relative levels of BAFF bound by each of the two antibodies in a sample, compared to the relative levels of BAFF bound by each of the two antibodies in a control is thus indicative of differences in BAFF levels and/or distribution in the biological sample.

Although certain embodiments of the invention are described in quantitative terms, the disclosed methods can include either quantitative or qualitative analysis, or both. Applicable techniques comprising contacting a biological sample with an antibody are well known in the art, and include enzyme linked immunosorbent assay (ELISA), fluorescence activated cell sorting (FACS™), immunohistochemistry, immunofluorescence, immunoprecipitation, western blotting, radioimmunoassay, enzyme multiplied immunoassay technique (EMIT), and affinity chromatography. Exemplary combinations of biological sample and analytical technique include, but are not limited to, analysis of serum by ELISA; analysis of blood by FACS™; and analysis of a tissue sample by immunohistochemistry.

In certain embodiments of the methods of the invention, the mammal has an immunological disorder. The term "immunologic disorder" refers to disorders and conditions in which an immune response is aberrant. The aberrant response can be due to (a) abnormal proliferation, maturation, survival, differentiation, or function of immune cells such as, for example, T and/or B cells. Examples of immunologic disorders include, but are not limited to, autoimmune diseases, B cell disorders including plasma cell disorders, lymphoproliferative immune disorders such as B cell neoplasias and B cell hyperplasias, antibody mediated disorders, transplant rejection, and allergies. According to one embodiment, the immunologic disorder is characterized by elevated BAFF levels.

Examples of autoimmune diseases include autoimmune rheumatologic disorders (e.g., rheumatoid arthritis, Sjogren's syndrome, scleroderma, lupus such as systemic lupus erythematosus (SLE) and lupus nephritis, polymyositis/dermatomyositis, cryoglobulinemia, anti-phospholipid antibody syndrome, psoriatic arthritis, ankylosing spondylitis), autoimmune gastrointestinal and liver disorders (e.g., inflammatory bowel diseases (e.g., ulcerative colitis and Crohn's disease), autoimmune gastritis and pernicious anemia, autoimmune hepatitis, primary biliary cirrhosis, primary sclerosing cholangitis, celiac disease), vasculitis (e.g., ANCA-associated vasculitis, Churg-Strauss vasculitis, Wegener's granulomatosis, and polyarteriitis), autoimmune neurological disorders (e.g., multiple sclerosis, opsoclonus myoclonus syndrome, myasthenia gravis, neuromyelitis optica, Parkinson's disease, Alzheimer's disease, autoimmune polyneuropathies, Guillian-Barre syndrome), autoimmune dermatologic disorders (e.g., psoriasis, urticaria, *pemphigus vulgaris*, bullous pemphigoid, cutaneous lupus erythematosus), autoimmune endocrine disorders (e.g., diabetic-related autoimmune diseases, insulin-dependent diabetes melitis (IDDM), Addison's disease, autoimmune thyroid disease (e.g., Graves' disease, thyroiditis such as Hashimoto's thyroiditis)), renal disorders (e.g., glomerulonephritis, Goodpasture's syndrome, Berger's disease), and hematologic disorders (e.g., thrombocytopenic purpura, thrombotic thrombocytopenic purpura, post-transfusion purpura, autoimmune hemolytic anemia.

Examples of hyperproliferative immune disorders include non-Hodgkin's lymphoma (NHL), chronic lymphocytic leukemia (CLL), acute lymphocytic leukemia (ALL), mantle cell lymphoma, marginal zone related tumors, follicular lymphoma (FL), large cell lymphoma such as diffuse large B-cell lymphoma, Burkitt's lymphoma, plasma cell disorders such as multiple myeloma.

Examples of antibody mediated pathologies include ITP, myasthenia gravis, autoimmune hemolytic anemia (erythrocyte autoantibodies), Hashimoto's thyroiditis (thyroid autoantibodies), myasthenia gravis (acetylcholine receptor autoantibodies), Graves' disease characterized by diffuse goiter and hyperthyroidism (thyrotropin receptor autoantibodies) and Goodpasture's syndrome comprising anti-GBM autoantibodies.

Other disorders that can be treated using the compositions and methods of the present invention include but are not limited to disorders described in PCT Publication WO 02/24909 and U.S. patent application Ser. Nos. 09/911,777; 10/380,703; 10/045,574; and 60/458,707.

It should be understood that particular diseases may fall under more than one category described above.

In certain embodiments of the methods, the control sample is one obtained from the same mammal prior to administration of the compound or composition to be tested. In some embodiments, the control sample is one obtained from the same mammal prior to the onset of disease. In some embodiments, the control sample is one obtained from a healthy mammal.

EXAMPLES

Example 1

Antibody Binding to BAFF Bound to Recombinant Receptor

ELISA plates (Costar™ 3369) were coated with 50 µl of 5 µg/ml BCMA-Fc, BR3-Fc, TACI-Fc, or Fn14-Fc (as a control Fc-fusion protein) in 50 mM sodium bicarbonate pH 9.6 and incubated overnight at 4° C. The coating solution was removed and the plate was blocked with 250 µl of 3% BSA in PBS (blocking buffer) at room temperature for 30 minutes. The wells were washed with 3×250 µl of 0.05% Tween 20 in PBS. Myc-tagged human BAFF, at a concentration of 0.5 ug/ml in blocking buffer, was added to each well and incubated for an hour at room temperature. After washing off the unbound myc-BAFF, 100 µl of 0.5 µg/ml biotinylated detection mAb (B4H7, A11C3 or A5E5, all previously known to bind free BAFF) or Fc-fusion protein (BCMA-Fc, BR3-Fc, TACI-Fc, or Fn14-Fc) was added and incubated at room temperature for 30 minutes. The wells were washed as described above and 100 µl of 0.5 µg/ml streptavidin HRP (Jackson ImmunoResearch) was added and incubated at room temperature for 30 minutes. The wells were washed as described and 100 µl of TMB substrate was added to the each well. The absorption was read at OD595 various times over 60 minutes.

As shown in Table 1, monoclonal antibody B4H7 binds to BAFF complexed with BCMA, TACI, or BR3. Other than weak binding of A5E5 to TACI-bound BAFF, neither of the other tested antibodies (A11C3 and A5E5) nor the receptors themselves bind to BAFF bound to receptor.

TABLE 1*

| Coated Protein | Detection protein | | | | | |
|---|---|---|---|---|---|---|
| | B4H7 | A11C3 | A5E5 | BCMA-Fc | BR3-Fc | TACI-Fc |
| BCMA-Fc | +++ | − | − | − | − | − |
| BR3-Fc | +++ | − | − | − | − | − |
| TACI-Fc | ++ | − | + | − | − | − |
| Fn14-Fc | − | − | − | − | − | − |

*(+) indicates relative levels of binding; (−) indicates no binding observed

Example 2

Antibody Binding to BAFF Bound to BJAB Cells Via BR3

This example illustrates the different abilities of two anti-BAFF monoclonal antibodies (mAb) to bind soluble BAFF bound to receptor expressed on the cell surface.

BJAB cells were incubated with 1 µg/ml biotin-labeled BAFF with BJAB cells (5×10$^6$ cells/ml) for 30 minutes on ice, washed with FACS buffer, and incubated with Streptavidin- PE (SA-PE) (Jackson ImmunoResearch) on ice for 30 minutes to visualize BAFF:BR3 interaction. To assess the ability of anti-BAFF mAbs (known to bind free BAFF) to bind to biotin-labeled BAFF after it has bound to BJAB cells via BR3, 1 µg/ml of biotin-labeled BAFF was incubated with BJAB cells ($5 \times 10^6$ cells/ml) for 30 minutes on ice, washed with FACS™ buffer, and incubated with control mouse IgG (10 µg/ml), anti-BAFF mAb A9C9 (10 µg/ml) or anti-BAFF mAb B4H7 (10 µg/ml), followed by anti-mouse IgG-PE (Jackson ImmunoResearch) for 30 minutes on ice. Unstained BJAB cells and cells incubated with biotin-labeled BAFF followed by control mouse IgG and anti-mouse IgG-PE were used as controls. As a final step, cells were washed in FACS buffer and fixed in 1% paraformaldehyde and evaluated on a FACsCaliber™ cell sorter for PE fluorescence.

As shown FIG. 1, the fluorescence signal for BAFF binding to BJAB cells was very bright (peak d), indicating that a significant amount of BAFF was bound to the cells. The anti-BAFF mAb B4H7 (peak e) detected most or all of the BAFF bound to its receptor on BJAB cells, while the anti-BAFF mAb A9C9 (peak c) gave a much lower fluorescence signal, indicating that A9C9 does not readily bind BAFF bound to receptor. The negative controls (peaks a and b) gave background signal.

The embodiments within the specification provide an illustration of embodiments of the invention and should not be construed to limit the scope of the invention. All publications and patents cited in this disclosure are incorporated by reference in their entirety. The citation of any references herein is not an admission that such references are prior art to the present invention. To the extent material incorporated by reference contradicts or is inconsistent with this specification, the specification will supersede any such reference.

What is claimed is:

1. A method of evaluating the distribution of BAFF, the method comprising:
    (a) contacting a first biological sample with a first anti-BAFF antibody, which binds BAFF independent of whether BAFF is bound to a receptor;
    (b) contacting a second biological sample, of the same type as the first, with a second anti-BAFF antibody, which preferentially binds free BAFF over BAFF bound to receptor; and
    (c) comparing the binding of the first antibody and the binding of the second antibody in the two samples,
wherein the comparison in (c) indicates the distribution of BAFF among various physiological pools in the samples.

2. A method of evaluating a compound or composition for the ability to modulate total BAFF in a mammal, the method comprising:
    (a) administering a test compound or composition to a mammal;
    (b) obtaining a biological sample from the mammal;
    (c) contacting the sample with an anti-BAFF antibody that binds BAFF independent of whether BAFF is bound to a receptor;
    (d) detecting the total amount of BAFF bound by the antibody in the biological sample; and
    (e) comparing the total amount of BAFF bound by the antibody in the biological sample with the amount of BAFF bound by the antibody in a control sample,
wherein a difference in binding attributable to the test compound or composition, indicates that the compound or composition is effective in modulating total BAFF in the mammal.

3. A method of evaluating a compound or composition for the ability to modulate the distribution of BAFF in a mammal, the method comprising:
    (a) administering a test compound or composition to a mammal;
    (b) obtaining a biological sample from the mammal;
    (c) contacting the sample with a first anti-BAFF antibody, which binds BAFF independent of its physiological state;
    (d) contacting the sample with a second anti-BAFF antibody, which preferentially binds free BAFF over BAFF bound to BAFF receptor;
    (e) detecting binding of the first antibody and the second antibody to BAFF in the sample; and
    (f) comparing the binding of the first antibody and the second antibody in the biological sample to the binding of the first and second antibodies in a control sample,
wherein a difference in binding attributable to the test compound indicates that the compound or composition is effective in modulating the distribution of BAFF in the mammal.

4. A method of evaluating a test compound or composition for the ability to modulate the distribution of BAFF, comprising:
    (a) administering a test compound or composition to a mammal;
    (b) obtaining a first biological sample and a second biological sample, both of the same type, from the mammal;
    (c) contacting the first biological sample with a first anti-BAFF antibody, which binds BAFF independent of whether BAFF is bound to a receptor;
    (d) contacting the second biological sample with a second anti-BAFF antibody, which preferentially binds free BAFF over BAFF bound to receptor;
    (e) detecting binding of the first antibody and the second antibody to BAFF in the two biological samples; and
    (f) comparing the binding of the first antibody and second antibody in the two biological samples to the binding of the first and second antibodies, respectively, in one or more control samples,
wherein a difference in binding attributable to the test compound or composition indicates that the compound or composition is effective in modulating the distribution of BAFF in the mammal.

5. The method of claim 1, wherein the biological samples are obtained from a mammal that has an autoimmune disease.

6. The method of claim 1, wherein the binding is evaluated qualitatively.

7. The method of claim 1, wherein the binding is evaluated quantitatively.

8. The method of claim 1, wherein the biological samples comprise serum and the method comprises ELISA.

9. The method of claim 1, wherein the biological samples comprise blood and the method comprises flow cytometry.

10. The method of claim 1, wherein the biological samples comprise tissue and the method comprises immunohistochemistry.

11. The method of claim 1, wherein the biological sample comprises serum, blood, plasma, biopsy sample, tissue sample, cell suspension, biological fluid, saliva, oral fluid, cerebrospinal fluid, amniotic fluid, milk, colostrum, mammary gland secretion, lymph, urine, sweat, lacrimal fluid, gastric fluid, synovial fluid, or mucus.

12. The method of claim 1, wherein the binding of the first anti-BAFF antibody indicates total BAFF.

13. The method of claim 1, wherein the binding of the second anti-BAFF antibody indicates free BAFF.

14. The method of claim 1, wherein the difference in binding of the first and second antibodies indicates receptor-bound BAFF in the sample.

15. The method of claim 2, wherein the control sample is obtained from the same mammal prior to administration of the compound or composition to be tested.

16. The method of claim 2, wherein the control sample is obtained from the same mammal prior to the onset of autoimmune disease.

17. The method of claim 2, wherein the control sample is obtained from a healthy mammal.

* * * * *

UNITED STATES PATENT AND TRADEMARK OFFICE
CERTIFICATE OF CORRECTION

| | | |
|---|---|---|
| PATENT NO. | : 9,097,726 B2 | Page 1 of 1 |
| APPLICATION NO. | : 14/179820 | |
| DATED | : August 4, 2015 | |
| INVENTOR(S) | : Yen-Ming Hsu and Susan Kalled | |

It is certified that error appears in the above-identified patent and that said Letters Patent is hereby corrected as shown below:

On the Title Page, after "Related U.S. Application Data", the paragraph labeled Item (62), is replaced with the following new paragraph:

(62) Division of application No. 13/791,293, filed on Mar. 8, 2013, now Pat. No. 8,685,657, which is a division of application No. 13/477,754, filed on May 22, 2012, now Pat. No. 8,415,111, which is a division of application No. 12/092,861 filed on June 27, 2008, now Pat. No. 8,202,698, which is a 371 of application No. PCT/US2006/043196 filed on Nov. 7, 2006.

Signed and Sealed this
Twenty-ninth Day of March, 2016

Michelle K. Lee
*Director of the United States Patent and Trademark Office*

UNITED STATES PATENT AND TRADEMARK OFFICE
CERTIFICATE OF CORRECTION

PATENT NO. : 9,097,726 B2  
APPLICATION NO. : 14/179820  
DATED : August 4, 2015  
INVENTOR(S) : Yen-Ming Hsu and Susan Kalled Page 1 of 1

It is certified that error appears in the above-identified patent and that said Letters Patent is hereby corrected as shown below:

On the Title page, item (71), Applicant: "Biogen Idec MA Inc., Cambridge, MA (US)" should read --Biogen MA Inc., Cambridge, MA (US)--.

Signed and Sealed this  
Second Day of August, 2016

Michelle K. Lee  
*Director of the United States Patent and Trademark Office*